United States Patent [19]

Blum et al.

[11] Patent Number: 4,784,135
[45] Date of Patent: Nov. 15, 1988

[54] FAR ULTRAVIOLET SURGICAL AND DENTAL PROCEDURES

[75] Inventors: Samuel E. Blum, White Plains; Rangaswamy Srinivasan, Ossining; James J. Wynne, Mt. Kisco, all of N.Y.

[73] Assignee: International Business Machines Corporation, Armonk, N.Y.

[21] Appl. No.: 894,520

[22] Filed: Aug. 11, 1986

Related U.S. Application Data

[63] Continuation of Ser. No. 448,123, Dec. 9, 1982, abandoned.

[51] Int. Cl.$^4$ ............................................. A61B 17/36
[52] U.S. Cl. ................................. 128/303.1; 128/395
[58] Field of Search .......................................... 128/4–8, 128/132 D, 303.1, 395–398, 633; 604/20, 22; 250/459.1, 461.1, 504 R; 362/32, 84, 259

[56] References Cited

U.S. PATENT DOCUMENTS

| | | | |
|---|---|---|---|
| 2,249,610 | 7/1941 | James et al. | 128/396 |
| 3,769,963 | 11/1973 | Goldman et al. | 128/665 |
| 3,769,983 | 11/1973 | Merav | 128/351 |
| 3,821,510 | 6/1974 | Muncheryan | 128/395 |
| 3,956,048 | 5/1976 | Nordgren | 128/132 D |
| 4,049,987 | 9/1977 | Helms | 250/504 |
| 4,273,110 | 6/1981 | Groux | 128/6 |
| 4,273,535 | 1/1981 | Yamamoto et al. | 128/303.1 |
| 4,316,467 | 2/1982 | Muckerheide | 128/303.1 |
| 4,388,924 | 6/1983 | Weissman et al. | 128/303.1 |

OTHER PUBLICATIONS

J. Taboada et al., *Health Physics*, 40, pp. 677–683, 1981, "Response of the Corneal Epithelium to KrF Excimer Laser Pulses".

J. Taboada et al., "An Extreme Sensitivity in the Corneal Epithelium . . . ", "Aerospace Medical Assoc. 1981, Meeting, San Antonio, TX.

"Ablative Photodecomposition: Action of Far-Ultraviolet (193 nm) Laser Radiation on Poly(Ethylene Teraphthilade) Films", Srinivasan and Leigh Dec. 1, 1982 *J. Am. Chem. Soc.* 1982, 104, 6784–6785.

*Primary Examiner*—Max Hindenburg
*Attorney, Agent, or Firm*—Jackson E. Stanland

[57] ABSTRACT

A method and apparatus are described for photoetching organic biological matter without requiring heat as the dominant etching mechanism. Far-ultraviolet radiation of wavelengths less than 200 nm are used to selectively remove organic biological material, where the radiation has an energy fluence sufficiently great to cause ablative photodecomposition. Either continuous wave or pulse radiation can be used, a suitable ultraviolet light source being an ArF excimer laser having an output at 193 nm. The exposed biological material is ablatively photodecomposed without heating or damage to the rest of the organic material. Medical and dental applications include the removal of damaged or unhealthy tissue from bone, removal of skin lesions, cutting or sectioning healthy tissue, and the treatment of decayed teeth.

21 Claims, 1 Drawing Sheet

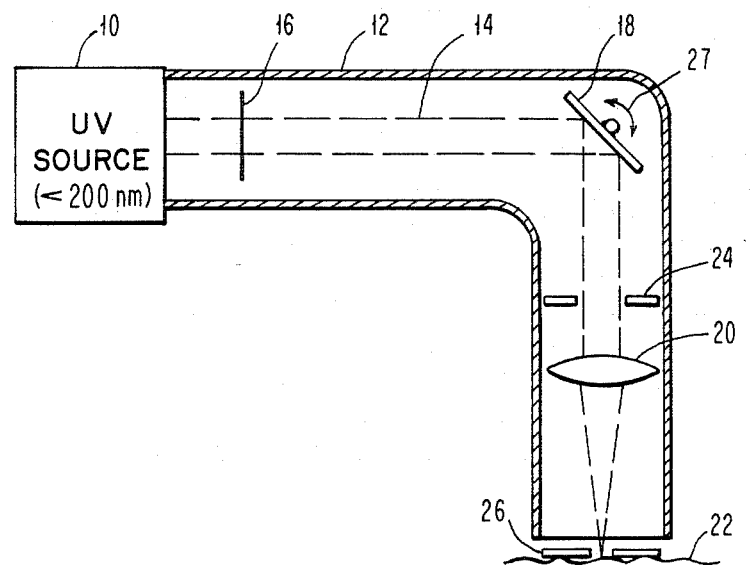

FAR ULTRAVIOLET SURGICAL AND DENTAL PROCEDURES

This application is a continuation of application Ser. No. 448,123, filed Dec. 9, 1982, now abandoned.

TECHNICAL FIELD

This invention relates to surgical and dental procedures using far ultraviolet radiation of wavelengths less than 200 nm, and more particularly to a method and apparatus for selectively removing organic material without heating and damage to surrounding organic material.

BACKGROUND ART

The use of radiation from lasers in medical and dental procedures has been known for some time, having been applied shortly after the invention of the laser in 1960. In 1961, medical researchers treated animal and human retinas and showed that a laser beam could induce a lesion on the retina for therapeutic purposes. Such laser eye surgery for detached retinas and other disorders is now routine in eye clinics throughout the world. In this application, and in others using laser beams, the laser beam is absorbed by the irradiated tissue causing heating, denaturing of protein, and tissue death. The results are therapeutic because of the formation of scar tissue, cauterization of the bleeding blood vessels, or the cutting away of diseased or damaged tissue.

Thus, in prior art applications of intense laser radiation, the laser was used to provide a directed source of the radiation whose thermal energy led to the pyrolysis of the organic matter. However, there are many situations where heating is not desired and is in fact harmful, and in those situations such lasers may not be used. As will be more apparent from the following, the present invention is directed to a technique for using radiation in a manner in which unnecessary heating and damage to surrounding organic tissue is avoided.

In the prior art, the intense laser radiation was generally in visible or infrared regions of the spectrum. For example, U.S. Pat. No. 3,769,963 describes an instrument for performing laser micro-surgery and describes the use of lasers for ophthalmology, dermatology, and experimental surgery. In this patent, a great deal of background information about laser treatments is provided, and the preferred wavelengths of light are stated to be 300–1000 nm although selective absorption of energy is noted in the range 200–3000 nm. In particular, selective absorption is noted in the visible range of 400–700 nm and in the infrared range at 1000 nm and 2000 nm.

Laser treatment of skin defects and lesions is described in U.S. Pat. No. 4,316,467 where a system is described for regulating the laser energy output in accordance with the absorption of the tissue being irradiated. Another reference describing lasers for medical and dental applications is U.S. Pat. No. 3,821,510. This patent describes a flexible laser beam transmitting device which can be held by hand and has certain adjustment features.

U.S. Pat. No. 4,273,535 describes a method for preventing tooth decay using giant pulses produced from a laser having an output wavelength of 1.06 micrometers (1060 nm). In particular, a flexible glass fiber is used as a laser beam guide for directing the laser energy from the laser source to the area to be irradiated.

In the prior art, the selectivity in absorption of different types of tissues has been noted, but the wavelengths used have been 200 nm and longer. Additionally, the only way to prevent irradiation (and its consequent damage) to nonselected areas surrounding the area selected for irradiation has been the use of a mask. Even with such a mask, heating of the target area is the primary mechanism for removal of organic matter. This means that surrounding areas will undergo some unavoidable heating and damage.

Accordingly, it is a primary object of this invention to provide an apparatus and method for efficient removal of organic biological material without heating or adverse effects to the areas of the material surrounding the area being irradiated.

It is another object of this invention to provide a technique and apparatus for removing organic biological material without using pyrolysis as the dominant mechanism for removal of the organic matter.

It is another object of the present invention to provide a technique and apparatus for decomposing an organic biological material by electronic excitation of the constituent bonds, followed by bond-breaking.

It is still another object of this invention to provide effective photoetching of the surface of biological material in a controlled manner.

It is a further object of this invention to provide a method and apparatus for photoetching the surface of organic materials in medical and dental applications.

It is another object of the present invention to provide focussed selective removal of organic matter, such as biological material, in a manner which does not require the use of heat, and without producing adverse thermal side effects.

It is another object of the present invention to provide a technique and apparatus for photoetching biological material which ablates the exposed surface of the material without significantly heating or otherwise damaging the remaining material, and without chemically altering the remaining material.

DISCLOSURE OF THE INVENTION

In its broadest sense, this invention relates to the use of ultraviolet radiation of wavelengths less than 200 nm for medical and dental purposes, and more particularly for etching or eroding biological organic material. The organic material can be selectively removed without undue heating and damage to the areas surrounding the area which is struck by the radiation. The mechanism by which the organic material is removed, or etched, is different than that of the prior art, and the geometry of the etching pattern is completely defined by the ultraviolet beam.

In the technique of this invention, ultraviolet radiation of less than 200 nm wavelength has a very high efficiency for decomposing organic biological matter by electronic excitation of the constituent bonds of the organic matter, followed by bond breaking. The organic material is removed by ablative photodecomposition without heating or otherwise damaging the remaining organic material. This is initially a relatively linear photochemical effect, and inhomogenities in the organic materials do not affect the photo etching.

This technique is useful for many different types of surgical and dental applications. For example, damaged or unhealthy tissue can be removed from bones without damaging the bone itself and without traumatizing the remaining tissue. Also, skin lesions can be removed without traumatizing any of the surrounding skin. Healthy tissue can be cut or sectioned by the technique of this invention, without heating the edges of the cut. This also minimizes trauma. In addition to these exemplary types of applications, the invention can be used to treat decayed teeth, removing dental carries while leaving enamel and healthy dentine unaltered, in a possibly painless manner.

The source of ultraviolet radiation can be any known source as long as the radiation is in the wavelength range less than 200 nm and as long as ablative photodecomposition occurs. Pulsed radiation of energy fluence at least about 10 mJ/cm$^2$/pulse is preferable, but continuous radiation can also be used. A suitable ultra-violet wavelength source is an ArF excimer laser providing a pulsed output at 193 nm. Such lasers are commercially available.

These and other objects, features, and advantages will be apparent from the following more particular description of the preferred embodiments.

BRIEF DESCRIPTION OF THE DRAWINGS

The FIGURE illustrates schematically one type of suitable apparatus for carrying out this invention.

BEST MODE FOR CARRYING OUT THE INVENTION

In the practice of this invention, ultraviolet radiation of wavelengths less than 200 nm is used to selectively remove organic material.

The radiation is applied either as pulsed radiation or as continuous wave radiation, and generally the pulsed radiation has a fluence greater than 10 mJ/cm$^2$/pulse. Ultraviolet radiation in this wavelength range does not burn organic materials such as human tissue; instead, it ablates the material, removing thin (micrometer) layers, layer by layer, for each pulse. In contrast, inorganic materials such as bone or tooth enamel are not photodecomposed by such radiation, at such energy densities.

Ultraviolet radiation having wavelengths less than 200 nm is capable of decomposing the organic material by electronically exciting the constituent bonds of the material, followed by bond-breaking and the production of volatile fragment materials which evaporate or escape from the surface. These photochemical reactions are particularly efficient for wavelengths less than 200 nm (i.e., vacuum ultraviolet radiation). In ablative photodecomposition, the broken fragments of biological matter require a larger volume than the unbroken chemical chains and "explode" from the biological matter, carrying away kinetic energy.

A suitable apparatus for carrying out the invention is shown in the FIGURE It includes a source 10 of ultraviolet radiation of wavelengths less than 200 nm. A suitable source is an ArF excimer laser operating at a wavelength of 193 nm. Such lasers are commercially available and are made by, for example, Lambda-Physik, W. Germany (a subsidiary of Coherent, Inc.). A specific laser with desirable properties for this application is the Lambda-Physik EMG-150 with an output of about 200 mJ/pulse, and a beam divergence of 200 microradians. These lasers routinely offer repetition rates of 60–100 pulses/second at an energy fluence greater than 200 millijoule/cm$^2$/pulse. The typical pulse duration is about 10 nsec.

A casing 12 is used to contain the laser beam 14 (indicated by the dashed lines). In a preferred embodiment, casing 12 is vented with nitrogen gas to remove oxygen from the beam path, since oxygen absorbs light at 193 nm.

Casing 12 includes a shutter 16 which can be used to block the radiation beam, or allow it to pass. Also included within casing 12 is a 100% reflecting mirror 18, which is used to change the direction of the ultraviolet radiation 14. A lens 20 is optional, and can be used to focus the radiation beam onto a selected spot of the organic material 22. An aperture 24 is located in front of lens 20 to provide further collimation of the radiation before it strikes lens 20. Also, a mask 26 optionally can be located on or close to the organic material 22 in order to more fully define the incident ultra-violet radiation.

In an actual instrument, casing 16 could be part of a moveable arm having articulated joints so that the radiation beam could be moved about, the end piece of the instrument being held in the surgeon's hand similarly to the holding of a scalpel. The instrument can also be moved relative to the patient, under the control of an alignment apparatus.

For the exact design of a suitable flexible casing, reference is made to aforementioned U.S. Pat. No. 3,769,963 which shows the use of an articulating arm and to aforementioned U.S. Pat. No. 3,821,510 which also shows a flexible laser-beam transmitting conduit that is capable of being held by hand. In addition to these references, aforementioned U.S. Pat. No. 4,316,467 describes a technique for regulating the output energy of a laser in accordance with the absorption of the incident radiation. If the apparatus is to be stationary, movement of the beam steering mirror 18 in the directions indicated by arrow 27, can be used to scan the radiation beam over a portion of the organic material to be etched.

The following will detail some examples of the medical and dental applications of the technique of the present invention. In a first application, bone surgery, ultraviolet radiation of wavelengths less than 200 nm is used to clean organic tissue from bone. In such surgery, it is usual to cut or scrape tissue from bone with scissors or scalpel. This prior art technique can traumatize the nearby healthy tissue resulting in swelling and unnecessary bleeding. To avoid these problems, ultraviolet light of wavelengths less than 200 nm and sufficient energy to ablatively photodecompose the tissue is focussed on the tissue to remove the tissue with great precision, without undesirable thermal effects. The tissue can be removed down to the bone without damaging the bone. This is because these wavelengths do not affect materials such as bone, which are many-fold less susceptible to ablative photoetching. Also, the inorganic bone surface is not affected by the laser energy fluence levels (10–300 mJ/cm$^2$/pulse) that effectively remove organic tissue.

In order to illustrate the advance of the present technique with respect to that of the prior art using lasers providing different wavelengths, grooves were cut into a piece of cartilage attached to a bone using, alternatively, ArF laser radiation at 193 nm and laser radiation from a frequency-doubled, pulsed Nd: YAG laser. The ArF excimer laser (193 nm) delivered pulses at approximately 100 mJ/pulse at 10 pulses per second for approximately five seconds. This laser light was focussed with a cylindrical lens and irradiated a line approximately 30 mil long and 0.3 millimeter wide. The energy fluence was about 1000 mJ/cm$^2$/pulse. This radiation produced a groove approximately 150 micrometers deep, with sharp edges and a uniform depth.

The frequency-doubled Nd:YAG laser delivered pulses at approximately 100 mJ/pulse at ten pulses per second for approximately five seconds. The wavelength was 532 nm, in the green portion of the visible spectrum. This laser was also focussed with a cylindrical lens to an area comparable to that illuminated by the ArF laser. Thus, the energy fluence produced by the two lasers were comparable.

In the case of the Nd:YAG laser, the line which was produced in the cartilage was very burned, and was comprised of burned-looking islands running approximately parallel to the clean groove which resulted from irradiation with the ArF laser. While the ArF laser at 193 nm cleanly removes cartilage, the frequency-doubled Nd:YAG laser charred the cartilage and produced raised carbonized islands.

Far-UV radiation in the wavelength range below 200 nm causes the cartilage tissue to undergo linear photochemistry in the first step of this process, and material inhomogeneities in the organic tissue are unimportant. In contrast with this, the photochemical effects are very nonlinear when visible wavelengths are used and inhomogeneities in the organic tissue play an important role in determining where the charred islands occur.

Another application of the technique and apparatus of this invention is the treatment of various skin defects. For example, port-wine scars (hemangiomas) and other types of birthmarks can be selectively removed by a bloodless surgical procedure, using the present invention. Here, the far-UV light is used to carefully remove thin layers of skin without undesirable thermal side effects and without undue bleeding.

For example, an ArF laser of the type shown can be used to excise skin cancer, remove port-wine scars, and remove "age" spots. Another application is the treatment of a common form of skin cancer, termed basal cell carcinoma. This type of cancer is often caused by damage from short wavelength ultraviolet light between 280–315 nm, such as that produced by sunlight. This wavelength region of sunlight produces sunburn and burning of the basal cell layer located between the epidermis and the dermis, and can result in basal cell carcinoma. When basal cell layer burning occurs, sometimes local areas undergo uncontrolled growth, which is the carcinoma. Longer ultraviolet wavelengths, between 315 and 400 nm, cause pigment darkening or "tanning" in the epidermis. This mechanism helps to protect the basal cell layer from burning.

A common technique for removing basal cell carcinoma involves scraping the skin at and around the lesion in order to take off layers of skin until all the malignant cells are removed. The dermatologist uses personal experience and "feel" as he scrapes the skin in layers, to determine when to stop scraping. In this procedure, the surrounding skin is often damaged and can become scarred in an unsightly manner over a larger area than is desirable.

When far-ultraviolet light surgery in accordance with the present invention is used, the carcinoma can be removed with a minimum of damage to healthy skin. The dermatologist uses the radiation beam to remove thin layers, layer by layer, and either uses his experience to determine when to stop, or uses some other chemical type of method. For example, the carcinoma may fluoresce differently than healthy skin under low-level long wavelength ultraviolet radiation. Since the skin removal process by ultraviolet radiation of wavelengths less than 200 nm is clean (i.e., no bleeding or scarring), it is easy to view the remaining tissue, unobscured by the roughened skin surface or by blood. This makes it easier to be able to tell when to stop removal of tissue.

Another application is in the field of dental medicine. Far-ultraviolet radiation of wavelengths less than 200 nm can be used to remove decay from teeth without damaging the surrounding enamel. As is known, teeth have an outside protective layer of calcium-based enamel. Decay is caused by bacterial action of food particles, particularly those containing sugar. This bacterial action produces lactic acid, which enters pores and cracks in the enamel and destroys the enamel to reach the organic dentine. A decay action then continues into the interior of the tooth toward the nerve. In the prior art, decay is treated by removing all of the decayed dentine and enamel, and filling the cavity with amalgam, gold, or some other nontoxic durable filler. The tooth is cleaned out with a mechanical drill, and much healthy enamel and dentine is also removed. The friction from the drilling produces heat and can be quite painful.

In contrast with this prior art technique, far-ultraviolet radiation of wavelengths less than 200 nm can be used to ablatively remove decay. In this technique the ultraviolet beam is focussed upon the decayed area of the tooth and photoetches the decay matter, producing volatile products which escape. The enamel will not be damaged, and the decayed dentine will be selectively eroded with no undesirable thermal side effects. This treatment may be entirely painless and can be used to limit the amount of area that is photoetched to exactly the area containing the decay. The apparatus shown can be used as a drill to selectively cut away the decayed dentine without "touching" the enamel which is to remain.

An additional use of this invention is in periodontal surgery. In this type of surgery, the gum tissue will be selectively eroded or cut, leaving the tooth enamel undamaged.

Another application for this invention is in cutting or sectioning healthy organic tissue without damaging the edges of the cut. Since undamaged tissue edges heal more neatly and safely than ragged edges or scarred tissues, the chance of infection or the presence of an unsightly scar is reduced.

In order to further demonstrate the degree of control over the etching process and the absence of heating effects, a sample of human hair was irradiated through a metal mask. Ablative photodecomposition of the hair was achieved by irradiating the human hair sample through a metal mask with 193 nm laser radiation. The energy fluence of the laser pulse was 250 mJ/cm$^2$/pulse. The rate of removal of the hair material was approximately 4000 Å per pulse, which is about threefold greater than the rates which have been realized when etching synthetic polymers with this radiation (as described in copending application Ser. No. 396,985, filed July 9, 1982, and assigned to the present assignee now U.S. Pat. No. 4,417,948). An enlarged view of the ablated material showed no evidence of thermal damage. In this irradiation, the hair was etched to controlled depths to provide rectangular grooves therein having sharply defined edges and uniform depth in each groove.

In the practice of this invention, organic biological material can be photodecomposed in an ablative process that produces volatile products that escape. The ultraviolet radiation source can be any source providing radiation of wavelengths less than 200 nm. The threshold energy flux for pulse radiation is about 10 mJ/cm$^2$/pulse. In this process, approximately 0.2 micrometers of organic tissue or other matter are removed by each radiation pulse having at least 10 mJ/cm$^2$/pulse. The pulse width of the incident ultraviolet radiation is not critical to the process and, in fact, continuous radiation may also be used.

The photodecomposition of the organic biological matter in this process is characterized by the absorption of a very large proportion (approximately 95%) of the incident photons in a thin (less than 2700 Å) layer of the organic material, and by the breaking of a large number of protein bonds in the material with a high (10–100%) quantum yield. Ejection of photolyzed material as small volatile molecules occurs into the surrounding atmosphere. These volatile or gaseous compounds typically have a low (less than 100) molecular weight. The irradiated surface is photoetched in a pattern that is defined by the light.

While it has been mentioned that both continuous wave radiation and pulsed radiation can be used in the practice of this invention, it may be that continuous wave radiation will be quite impractical. In the situation where continuous wave radiation is used, the bonds in the biological layer of organic matter may be broken but may recombine and deposit again if the process proceeds too slowly. Using a pulse radiation source means that a large amount of energy can be delivered in a very small amount of time. When this occurs, the bonds are broken in the biological layer in a short amount of time, pressure is built up, and volatile products blow off. This is the mechanism of ablative photodecomposition (APD), which requires that the broken fragments be produced in a small volume in a sufficiently short time that they blow off due to the pressure build-up. The radiation source must provide this type of power density for ADP to occur.

In the first step, the photochemistry is linear, the bonds being broken by the incident radiation. However, the blow-off of volatile products is a nonlinear function of the rate at which the energy is introduced into the biological layer. In the example given previously, a minimum energy flux of about 10 mJ/cm$^2$/pulse is sufficient to provide ablative photochemistry in which volatile products are blown off after the pulse (which is about 10 nsec. wide) is applied.

The wavelength of the incident ultraviolet radiation is chosen to be less than 200 nm, and generally extends down to about 100 nm. In the spectroscopic art, this is termed the vacuum ultraviolet range, and generally comprises those wavelengths which begin to be absorbed in air. For example, oxygen begins to absorb radiation at about 200 nm, and this is why the apparatus shown is vented with nitrogen. As the wavelength decreases, more and more absorption will occur by different gases.

Upon absorption of radiation in the wavelength range 100–200 nm, only a thin layer of the tissue is ablatively photodecomposed, and the radiation will not penetrate and damage other portions of the tissue. In contrast with this, longer wavelength radiation will produce burning and will not be characterized by ablative photodecomposition.

In addition to the reasons described above for choosing the appropriate wavelength range, another practical reason exists with respect to the apparatus. It is known that lithium fluoride can be used as a transmission window located adjacent to the laser radiation source. Lithium fluoride has the shortest wavelength of transmission, and will cut off at approximately 110 nm. That is, at wavelengths shorter than 110 nm, the lithium flouride will not be transparent.

Thus, for wavelengths less than 110 nm, a lithium fluoride window cannot be used, and the laser output would have to be passed through a vacuum chamber in order to prevent large amounts of absorption of the radiation. This would be a complex and costly apparatus. Also, no optical fiber is known which can transmit radiation at wavelengths less than 110 nm.

Thus far, an ablative photodecomposition process has been described in which no heat effects are produced. That is, the photochemistry is such that the energy in the incident ultraviolet radiation is transmitted to the kinetic energy of the volatile products leaving the biological layer that is irradiated. The energy which is present in the ultraviolet beam is not transmitted as heat to the biological layer. This has been confirmed by measurements which look at the morphology of the material. Additionally, it is an effect which can be readily felt. As an example, a person can place his hand in the path of ultraviolet radiation having wavelengths less than 200 nm, and experience no pain. Only a small "pressure" is felt when the volatile gases are blown off, the pressure being a recoil when these gases blow off.

While the ablative photodecomposition intended by the process of the present invention does not lead to a noticeable heat buildup in the biological layer, it is obvious that heat will begin to occur if more and more energy is applied. That is, when the amount of energy supplied is greater than the amount which can be carried away by the volatile byproducts, some heating will begin to occur.

The minimum energy flux for producing ablative photodecomposition of these biological layers is about 10 mJ/cm$^2$/pulse, and the maximum energy for practical purposes is that which begins to cause detrimental heating and other effects similar to those which are seen when radiation of wavelengths greater than 200 nm is applied. This maximum amount of input energy flux depends upon the particular type of biological layer being photodecomposed in accordance with the present invention. Generally, it is desired that no significant amount of heating should occur in either the medical or dental applications of this invention. However, in its broadest sense the invention relates to ablative photodecomposition of biological layers at wavelengths less than 200 nm. For pulsed radiation, this effect begins to occur if the input energy flux is at least about 10 mJ/cm$^2$/pulse.

As a corollary to the fact that heat is not produced when the input energy flux is not unduly great, it has been noted that a pulsed beam of radiation from a YAG laser operating at the same power level will cause the sensation of pain to a human, while ultraviolet radiation at wavelengths less than 200 nm will not cause this sensation of pain. Of course, the reason is straightforward and is due to the difference between ablative photodecomposition in accordance with the present invention and decomposition resulting from a burning effect as is experienced in the prior art.

Using ultraviolet radiation of wavelengths less than 200 nm has yielded ablative photodecomposition of biological matter without noticeable pyrolytic heat effects (i.e., chemical changes induced by heat) at energy fluxes up to about 1000 mJ/cm$^2$/pulse, although this is not necessarily an upper limit.

In the practice of this invention, any type of medical or dental application can be undertaken using ablative photodecomposition at wavelengths less than 200 nm. While the invention has been particularly described with respect to certain embodiments and applications, it will be readily apparent to those of skill in the art that other applications can be made without departing from the spirit and scope of the invention. Further, the exact apparatus for transmitting the ultraviolet radiation to the organic matter to be photodecomposed can be varied by those of skill in the art, without departing from the spirit and scope of this invention.

We claim:

1. A method for removing selected areas of a biological layer comprised of organic material, including the steps of:
   selecting a desired area of said biological layer, and
   irradiating said desired area with a plurality of pulses of pulsed ultraviolet radiation having wavelengths less than 200 nanometers and energy fluences sufficient to cause ablative photodecomposition of said biological layer to an optically visible depth, said pulses having energy fluences per pulse at least about 10 mJ/cm$^2$, the pulse fluence, pulse width and pulse repetition rate of said pulses being sufficiently small that no substantial accumulation of heat occurs in areas of said biological layer adjacent said desired area.

2. The method of claim 1, where said ultraviolet radiation is passed through a mask before striking said biological layer.

3. The method of claim 1, where said biological layer is a layer of human tissue.

4. The method of claim 1, where said biological layer is an organic layer located in teeth.

5. The method of claim 1, where said ultraviolet radiation is produced by an ArF laser emitting pulses at 193 nm.

6. The method of claim 1, where the wavelength of said ultraviolet radiation is chosen to photodecompose human protein layers while not decomposing enamel and bone.

7. The method of claim 1, where said ultraviolet radiation is focussed onto a small area of said biological layer.

8. The method of claim 1, where said ultraviolet radiation is present in a beam which is scanned over a selected area of said biological layer.

9. A method for selectively removing portions of a biological layer comprised of an organic material, comprising the steps of:
   selecting an area of said biological layer for irradiation by ultraviolet radiation, and irradiating said selected area with a plurality of pulses of pulsed ultraviolet radiation having wavelengths less than 200 nm, said radiation being produced by a laser and having a minimum energy flux of about 10 mJ/cm$^2$/pulse, said radiation causing photodecomposition of said selected area by ablation of surface regions of said selected area in a manner in which volatile by-products are blown off without diffusion of substantial amounts of heat into the regions of said biological layer surrounding said selected area to etch said area to a depth which is optically visible, the pulse fluence, pulse width and pulse repetition rate of said laser pulses being sufficiently small that no substantial accumulation of heat occurs in regions of the biological layer surrounding said selected area.

10. The method of claim 9, where said biological layer is comprised of protein organic material.

11. The method of claim 10, where said biological layer is human organic matter.

12. The method of claim 11, where said ultraviolet radiation is scanned across a selected region of said biological layer.

13. A method for removing a selected amount of a biological layer comprised of organic material, including the steps of:
   selecting a desired area of said biological layer, irradiating said desired area with pulses of ultraviolet radiation from a laser providing pulsed radiation that is substantially absorbed in a thin region of said biological layer, said pulsed radiation having an energy fluence sufficiently great to cause the production of volatile species localized in the area struck by said laser pulses without diffusion of a substantial amount of heat into said biological layer to etch said biological layer in said area, said volatile products being produced and blown off substantially only along the optical path of said laser pulses in said biological layer,
   said pulses of radiation having energy fluences per pulse at least about 10 mJ/cm$^2$, the pulse fluence, pulse width and pulse repetition rate of said pulses being sufficiently small that no substantial accumulation of heat occurs in regions of said biological layer surrounding said desired area, and
   continuing the irradiation of said biological layer for time period sufficient to insure that said selected mount of the biological material is removed, said etched area being sufficiently deep that it is optically visible.

14. The method of claim 13 where said biological layer is comprised of living organic tissue.

15. The method of claim 14, where said living organic tissue is a layer of human tissue.

16. The method of claim 13, where said laser pulses are scanned across a selected region of said biological layer.

17. A method for removing a portion of a biological layer comprised of protein organic material, comprising the step of:
   irradiating a selected area of said layer by a plurality of pulses of ultraviolet laser radiation which are absorbed in a small depth of said biological layer, said pulsed radiation having an energy fluence per pulse sufficient to cause the production of volatile species in said selected area in a time period which is short compared to the time required for energy to diffuse into regions of said biological layer surrounding said selected area, said volatile species escaping from said biological layer to produce etching in said selected area to an optically visible depth, said energy fluence being at least about 10 mJ/cm$^2$/pulse, the pulse width and pulse repetition rate of said pulses being sufficiently small that no substantial heating occurs in regions of said protein organic material adjacent said selected area.

18. The method of claim 17, where said laser radiation is produced by an excimer laser.

19. A method for removing a portion of a protein biological layer to a desired depth, comprising the steps of:

directing a plurality of pulses of ultraviolet radiation at said biological layer, said pulses being absorbed in a small depth of said biological layer and having an energy intensity in excess of a threshold amount necessary to etch said biological layer by a process in which volatile species are produced in the area of said biological layer struck by said pulses and escape therefrom to cause said etching, said volatile species being produced in a time period that is short compared to the time required for energy to diffuse into said biological layer, said pulses having energy fluences per pulse at least about 10 mJ/cm$^2$, the pulse fluence, pulse width and pulse repetition rate of said pulses being sufficiently small that no substantial accumulation of heat occurs in regions of said biological layer surrounding the area irradiated by said pulses, and continuing the irradiation of said biological layer by said pulses until removal of said portion of the biological layer is complete to a depth which is optically visible.

20. The method of claim 19, where said pulses are produced by an excimer laser.

21. A method for etching a biological sample to an optically visible depth, comprising the steps of:

delivering energy to a small volume of said biological sample by irradiating said sample with a plurality of ultraviolet laser pulses, said laser pulses having energy fluences per pulse at least about 10 mJ/cm$^2$, the pulse fluence, pulse width and pulse repetition rate of said pulses being sufficiently small that no substantial accumulation of heat occurs in regions of said biological sample adjacent to the location where said laser pulses are absorbed.

* * * * *